United States Patent
Cambron et al.

(10) Patent No.: US 6,537,495 B1
(45) Date of Patent: Mar. 25, 2003

(54) VACUUM-ASSISTED VENOUS DRAINAGE SYSTEM WITH RIGID HOUSING AND FLEXIBLE RESERVOIR

(75) Inventors: Ronald Cambron, Laguna Hills, CA (US); Francis Vijay, Lake Forest, CA (US); Richard Knight, Huntington Beach, CA (US); Ken Litzie, Irvine, CA (US)

(73) Assignee: Edwards Lifesciences LLC

( * ) Notice: Subject to any disclaimer, the term of this patent is extended or adjusted under 35 U.S.C. 154(b) by 0 days.

(21) Appl. No.: 09/472,093

(22) Filed: Dec. 23, 1999

Related U.S. Application Data

(62) Division of application No. 08/938,058, filed on Sep. 26, 1997, now Pat. No. 6,017,493.

(51) Int. Cl.$^7$ .......................... A61M 1/14; A61M 1/36; A61M 37/00
(52) U.S. Cl. ...................... 422/45; 604/6.14; 604/6.16; 604/4.01; 128/DIG. 3
(58) Field of Search .................. 604/4.01, 5.01, 604/6.01, 6.1, 6.11, 6.13, 6.14, 6.16, 65–7, 131, 149–51, 403, 6.15; 422/44–48; 128/DIG. 24, DIG. 3; 210/416.1

(56) References Cited

U.S. PATENT DOCUMENTS 3,890,969 A    6/1975  Fischel (List continued on next page.)

FOREIGN PATENT DOCUMENTS

| DE | 4326886 A1 | 2/1995 |
|---|---|---|
| EP | 0 112 641 B1 | 6/1986 |
| EP | 0 096 195 B1 | 9/1986 |
| EP | 0 111 087 B1 | 6/1987 |
| EP | 0 094 682 B1 | 11/1987 |
| EP | 0 309 642 A1 | 4/1989 |
| EP | 0 320 815 A2 | 6/1989 |

(List continued on next page.)

OTHER PUBLICATIONS de Jong, et al., "Hematologic Aspects of Cardiotomy Suction in Cardiac Operations", J Thorac Cardiovasc Surg, vol. 79, No. 2, pp. 227–236, Feb. 1980.

(List continued on next page.)

*Primary Examiner*—Angela D. Sykes
*Assistant Examiner*—Patricia Bianco
(74) *Attorney, Agent, or Firm*—Debra D. Condino; John Christopher James

(57) ABSTRACT

A vacuum-assisted venous drainage reservoir for cardiopulmonary bypass surgery with both hard and soft shell reservoirs. The system utilizes a wall vacuum or other source of negative pressure to create a negative pressure via a regulator within a sealed hard shell reservoir, or within a sealed housing surrounding a soft shell reservoir. The addition of a negative pressure in the venous return line enables the use of smaller cannulas suitable for minimally invasive surgery. The reservoir need not be positioned well below the patient as in conventional gravity venous drainage configurations, thus adding flexibility to the operating room layout and enabling a reduction in the extracorporeal blood prime volume needed. In one embodiment, a flexible membrane in the hard shell reservoir expands to contact the blood surface and reduce blood/air interactions. In another embodiment, a moisture trap is provided between the source of vacuum and hard shell reservoir to reduce environmental contamination. A volume sensor for the hard shell reservoir may be used in a feedback loop for controlling the vacuum, circulation pump, or other device. A pressure relief valve may be included in both systems for safety, and a vacuum stabilizer reduces the severity of large changes in vacuum pressure. A piece of air-permeable material may form a portion of the soft shell reservoir to vent air from within.

5 Claims, 8 Drawing Sheets

U.S. PATENT DOCUMENTS

| | | | |
|---|---|---|---|
| 3,896,733 A | 7/1975 | Rosenberg | |
| 4,131,431 A | 12/1978 | Siposs | |
| 4,205,677 A | 6/1980 | Engstrom | |
| 4,243,531 A | 1/1981 | Crockett et al. | |
| 4,402,687 A | 9/1983 | Denty et al. | |
| 4,416,658 A | 11/1983 | Numazawa et al. | |
| 4,435,171 A | 3/1984 | Goldberg et al. | |
| 4,443,220 A | 4/1984 | Hauer et al. | |
| 4,466,888 A | 8/1984 | Verkaart | |
| 4,490,331 A | 12/1984 | Steg, Jr. | |
| 4,540,399 A | 9/1985 | Litzie et al. | |
| 4,573,992 A | 3/1986 | Marx | |
| 4,599,093 A | 7/1986 | Steg, Jr. | |
| 4,610,656 A | 9/1986 | Mortensen | |
| 4,671,786 A | 6/1987 | Krug | |
| 4,734,269 A | 3/1988 | Clarke et al. | |
| 4,744,785 A | 5/1988 | Rosenthal et al. | |
| 4,828,543 A | 5/1989 | Weiss et al. | |
| 4,923,438 A | 5/1990 | Vasconcellos et al. | |
| 4,959,062 A | 9/1990 | Gellman | |
| 4,964,849 A | 10/1990 | Robicsek | |
| 5,011,470 A | 4/1991 | Kurtz et al. | |
| 5,019,060 A | 5/1991 | Goosen | |
| 5,024,613 A | 6/1991 | Vasconcellos et al. | |
| 5,035,865 A | 7/1991 | Inaba et al. | |
| 5,039,482 A | 8/1991 | Panzani et al. | |
| 5,049,146 A | 9/1991 | Bringham et al. | |
| 5,055,198 A | 10/1991 | Shettigar | |
| 5,061,236 A | 10/1991 | Sutherland et al. | |
| 5,078,677 A * | 1/1992 | Gentelia et al. | 604/317 |
| 5,087,250 A | 2/1992 | Lichte et al. | |
| 5,141,504 A | 8/1992 | Herweck et al. | |
| 5,158,533 A | 10/1992 | Strauss et al. | |
| 5,158,534 A | 10/1992 | Berry et al. | |
| 5,188,604 A | 2/1993 | Orth | |
| 5,201,703 A | 4/1993 | Gentelia et al. | |
| 5,215,519 A | 6/1993 | Shettigar | |
| 5,270,005 A | 12/1993 | Raible | |
| 5,275,585 A | 1/1994 | Olson | |
| 5,281,112 A | 1/1994 | Montoya et al. | |
| 5,300,015 A | 4/1994 | Runge | |
| 5,303,585 A | 4/1994 | Lichte | |
| 5,305,982 A | 4/1994 | Tamari | |
| 5,312,589 A | 5/1994 | Reeder et al. | |
| 5,336,051 A | 8/1994 | Tamari | |
| 5,342,182 A | 8/1994 | Montoya et al. | |
| 5,372,593 A | 12/1994 | Boehringer et al. | |
| 5,378,227 A | 1/1995 | O'Riordan et al. | |
| 5,382,227 A | 1/1995 | Riquier | |
| 5,411,472 A | 5/1995 | Steg, Jr. et al. | |
| 5,411,705 A | 5/1995 | Thor et al. | |
| 5,411,706 A | 5/1995 | Hubbard et al. | |
| 5,419,769 A | 5/1995 | Devlin et al. | |
| 5,423,780 A | 6/1995 | Malette | |
| 5,437,651 A | 8/1995 | Todd et al. | |
| 5,478,309 A | 12/1995 | Sweezer et al. | |
| 5,484,428 A | 1/1996 | Drainville et al. | |
| 5,487,727 A | 1/1996 | Snider et al. | |
| 5,507,734 A | 4/1996 | Everett, Jr. et al. | |
| 5,512,042 A | 4/1996 | Montoya et al. | |
| 5,571,081 A | 11/1996 | Adhoute | |
| 5,573,526 A * | 11/1996 | Hess | 128/DIG. 3 |
| 5,586,085 A | 12/1996 | Lichte | |
| 5,588,958 A | 12/1996 | Cunningham et al. | |
| 5,599,333 A | 2/1997 | Atkinson | |
| 5,607,411 A | 3/1997 | Heironimus et al. | |
| 5,823,986 A | 10/1998 | Peterson | |
| 6,017,493 A * | 1/2000 | Cambron et al. | 422/44 |
| 6,315,751 B1 * | 11/2001 | Cosgrove et al. | 422/45 |

FOREIGN PATENT DOCUMENTS

| | | |
|---|---|---|
| EP | 0 156 110 B1 | 10/1989 |
| EP | 0 357 338 A2 | 3/1990 |
| EP | 0 384 585 B1 | 8/1990 |
| EP | 0 400 518 A2 | 12/1990 |
| EP | 0 201 528 B1 | 5/1991 |
| EP | 0 438 703 B1 | 7/1991 |
| EP | 0 583 148 A2 | 2/1994 |
| EP | 0 617 627 B1 | 10/1994 |
| EP | 0 450 132 B1 | 9/1995 |
| EP | 0 743 071 A2 | 11/1996 |
| EP | 0 786 974 A2 | 4/1997 |
| EP | 0 786 261 | 7/1997 |
| RU | 2 088 022 C1 | 2/1994 |
| WO | WO 84/03838 | 10/1984 |
| WO | WO 92/20380 | 11/1992 |
| WO | WO 93/11808 | 6/1993 |
| WO | WO 96/24397 | 8/1996 |

OTHER PUBLICATIONS

OTHER PUBLICATIONS

Hirose et al., "Reduction of Perfusion Hemolysis by the Use of Atraumatic Low–Pressure Suction", J Thoracic and Cardiovasc Surg, vol. 47, No. 2, pp. 242–247, Feb. 1964.

Hiroura, et al., "Trial of Roller Pump–less Cardiopulmonary Bypass System", pp. 1–14, date unknown.

Koyama et al., "Usefulness of 'Low–Vacuum Suction Method' for Cardiopulmonary Bypass", pp. 595–599, Feb. 24, 1995.

Pearson, et al., "An Ultrasonic Analysis of the Comparative Efficiency of Various Cardiotomy Reservoirs and Micropore Blood Filters", THORAX, vol. 33, pp. 352–358, 1978.

Wright, et al., "Cellular Aggregation and Trauma in Cardiotomy Suction Systems", THORAX, vol. 34, pp. 621–628, 1979.

Baxter Product Information Document (PID), "HSR4000 Venous Reservoir with Cardiotomy Autotransfusion Filter".

Galletti, et al. "Principles and Techniques of Extracorporeal Circulation", *Heart–Lung Bypass*, p. 174–179.

Kirklin, et al. "Morphology, Diagnostic Criteria, Natural History, Techniques, Results, and Indications", *Cardiac Surgery* vol. 1, Part 1 General Considerations, p. 76.

Sistino et al. "Laboratory Evaluation of a Low Prime Closed–Circuit Cardiopulmonary Bypass System", *The Journal of Extra–Corporeal Technology*, vol. 24 No. 4, 1993, p. 116–119.

* cited by examiner

VACUUM-ASSISTED VENOUS DRAINAGE SYSTEM WITH RIGID HOUSING AND FLEXIBLE RESERVOIR

RELATED CASES

The is a divisional application Ser. No. 08/938,058 filed Sep. 26, 1997, which is now U.S. Pat. No. 6,017,493.

FIELD OF THE INVENTION

The present invention relates generally to reduced prime volume cardiopulmonary bypass systems and, more particularly, to vacuum-assisted venous drainage systems and methods.

BACKGROUND OF THE INVENTION

Cardiopulmonary bypass (CPB) surgery requires a perfusion system, or heart-lung machine, to maintain an adequate supply of oxygen in the patient's blood during the surgery. An example of such a perfusion system is shown in FIG. 1. A venous return cannula is inserted in one of the veins leading directly to the heart and receives the "used" blood for rejuvenation through the perfusion system. The blood flows along a conduit (typically a transparent flexible tube) to a venous reservoir which may be combined with a cardiotomy reservoir. Commonly, a sucker extracts excess fluid from the chest cavity during the operation and diverts the fluid, which may contain bone chips or other particulates, into the top of the cardiotomy reservoir. The cardiotomy sucker pulls pooled blood from the chest cavity using a vacuum which may be generated by a roller pump, for example. In addition, a vent cannula may be positioned in the heart for suctioning other fluids during the operation, those fluids also being directed to the cardiotomy reservoir through a roller pump. The fluid entering the cardiotomy reservoir is first filtered before being combined with the venous blood.

In contrast to the suction within the cardiotomy and vent lines, the venous return cannula is positioned in a vein in contact with a relatively constant stream of blood. Thus, the conventional venous drain method is to place the reservoir under the patient and allow blood to drain by gravity. This method is facilitated by the relatively large bore venous return cannulas of 36 French OD or more used in open heart surgery. A major drawback to the gravity drain, however, is that the system must be primed before a return pump can take effect. The only means of enhancing venous return is by increasing the head height between the cannula and the venous reservoir. This is achieved either by lowering the location of the reservoir, limited by the floor, and/or by raising the level of the operating table, both which are limited.

Blood is pumped by a centrifugal or roller pump, for example, from the venous/cardiotomy reservoir through a blood oxygenator and back to the patient. The pump assumes the pumping task of the heart and perfuses the patient's circulatory system. The oxygenator typically directs a flow of blood across a plurality of permeable fibers which are capable of transferring oxygen to and carbon dioxide from the blood. The oxygenator also usually includes a heat exchange system to regulate the extacorporeal blood temperature. Before reaching the patient, the blood may pass through a temperature control monitoring system and along a conduit through an arterial filter and bubble detector, before reaching an arterial cannula positioned in a main artery of the patient.

The perfusion system is typically mounted on a table positioned some distance from the operating table. Thus, the conduits leading from the patient to the various components of the perfusion system contain a significant volume of blood. In addition, the various components such as the venous cardiotomy reservoir and arterial filter also require a certain volume of blood to function properly. All of these components put together require a certain "prime" or volume of blood from the patient to function. The prime volume can be defined as that volume of blood outside the patient, or extracorporeal.

The need for a large prime volume is contrary to the best interest of the patient who is undergoing the surgery and is in need of a minimum supply of fully oxygenated blood. Therefore, a significant amount of research and development has been directed toward reducing the prime volume within CPB systems. Some of the areas in which such a reduction of volume can be attained is to reduce the volume of the components, such as the venous cardiotomy reservoir, or blood oxygenator. Another means for reducing the volume of the system is to position the perfusion setup closer to the patient. One specific example of a CPB system for reducing prime is disclosed in U.S. Pat. No. 5,300,015 to Runge. The Runge circuit eliminates conventional blood reservoirs and utilizes a pulsatile pump which compresses a flexible blood conduit to urge blood therethrough. Although prime is reduced, the perfusionist can not view a reservoir level to help regulate the proper flow of blood to and from the patient.

A new type of perfusion system uses a vacuum in conjunction with gravity to drain blood from the venous system. One such configuration is the subject of a paper entitled "Trial of Roller Pump-Less Cardiopulmonary Bypass System" by Hiroura, et al. of the Department of Thoracic Surgery, Nagoya University School of Medicine, published in conjunction with Owari Prefectural Hospital, both in Aichi, Japan. This reference discloses a system in which a wall vacuum generates a negative pressure of between −5 and −35 mmHg within a main reservoir, which is connected to a plurality of individual suction reservoirs and to a venous return line. Cardiotomy and other suction lines from the patient are attached to the individual suction reservoirs, and the vacuum pressure within each one of the suction reservoirs can be regulated independently. The system further includes a centrifugal pump under the main reservoir for pumping blood through the rest of the CPB system and to the patient. A significant amount of hardware is needed for this system to regulate and connect the various pressure chambers.

There exists a need for a reduced prime CPB system which may make use of existing hardware and minimizes trauma to the blood.

SUMMARY OF THE INVENTION

In a preferred embodiment, the present invention provides a vacuum assisted venous drainage system, comprising: a reservoir for receiving blood from a venous system of a patient; a source of vacuum; a conduit extending between the source of vacuum and configured to create a negative pressure within the reservoir; a pressure regulator in the conduit; and a vacuum stabilizer positioned in the conduit between the pressure regulator and the reservoir, the vacuum stabilizer allowing air into the conduit from the exterior thereof to modulate extreme changes in pressure within the conduit, but preventing air from escaping from the conduit.

In another embodiment, a vacuum assisted venous drainage system is provided, comprising: a hard shell venous reservoir for receiving blood from a venous system of a patient; a source of vacuum; a conduit extending between the source of vacuum and configured to create a negative pressure within the reservoir; a pressure regulator in the conduit; and a moisture trap in fluid communication with the conduit between the pressure regulator and the hard shell reservoir, the moisture trap serving to collect fluids drawn from the reservoir before reaching the pressure regulator.

In a further embodiment, the invention discloses a method of surgery, comprising: securing a first cannula percutaneously in a patient; securing a second cannula percutaneously in a patient; connecting the first cannula to a venous reservoir blood inlet port; creating a negative pressure in the venous reservoir; regulating the pressure within the venous reservoir; and pumping blood from the venous reservoir through a blood oxygenator and to the second cannula back to the patient.

Another aspect of the present invention is a reduced blood/air interface venous reservoir, comprising: a rigid container having an inlet adapted to receive venous blood into an interior space sealed from the atmosphere, the container shaped to contain the blood and form a blood surface; an outlet in the rigid container adapted to drain blood to an extracorporeal oxygenation circuit; a vacuum port in the reservoir adapted to be connected to a source of vacuum; and a flexible air impermeable membrane mounted within the container and defining a closed space sealed from the interior space of the container, the membrane having sufficient flexibility so that the closed space expands into the interior space upon a vacuum being drawn within the container, the membrane configured to expand and contact the blood surface.

Another method provided by the present invention is a method of collecting blood within a venous reservoir to reduce the blood/air interface, comprising: supplying blood to an inlet port of a reservoir having a rigid outer container defining an inner space sealed from the atmosphere, the container being shaped to channel the blood and for a blood surface; drawing a vacuum within the rigid outer container; providing a flexible membrane attached within the rigid container and defining a closed space sealed from the container inner space, so that the closed space expands into the interior space upon a vacuum being drawn within the container, the membrane configured to expand and contact the blood surface; and draining the blood from the container through an outlet port.

The present invention is also embodied in a vacuum assisted venous reservoir, comprising: a rigid, sealed outer housing; a flexible, blood impermeable reservoir within the housing; an inlet port in the reservoir; a conduit attached to the inlet port and in communication with the interior of the reservoir, the conduit passing through a sealed opening in the housing and being connected to a source of venous blood; a vacuum conduit extending between a source of vacuum and the interior of the housing through a sealed opening; and a pressure regulator between the vacuum conduit and vacuum source.

Further objects and advantages of the present invention shall become apparent to those skilled in the art upon reading and understanding the following detailed description of a presently preferred embodiment of the invention.

DESCRIPTION OF THE PREFERRED EMBODIMENTS

The present invention provides vacuum-assisted venous drainage into reservoirs of various types. As shown and described herein, both hard- and soft-shelled reservoirs may be used, although those of skill in the art will recognize that various other types of reservoirs may also be adapted for vacuum-assisted drainage. Furthermore, the reservoirs as depicted in the present invention are combined cardiotomy and venous reservoirs, but venous reservoirs separate from cardiotomy reservoirs may also be adapted for vacuum-assisted drainage. Finally, various components of conventional cardiopulmonary bypass systems may be used with the vacuum-assisted venous drainage reservoirs of the present invention, so that those illustrated are not to be considered limiting, and any other conventional components typically used in CPB systems and omitted from the description and drawings may be included.

Figure 1:
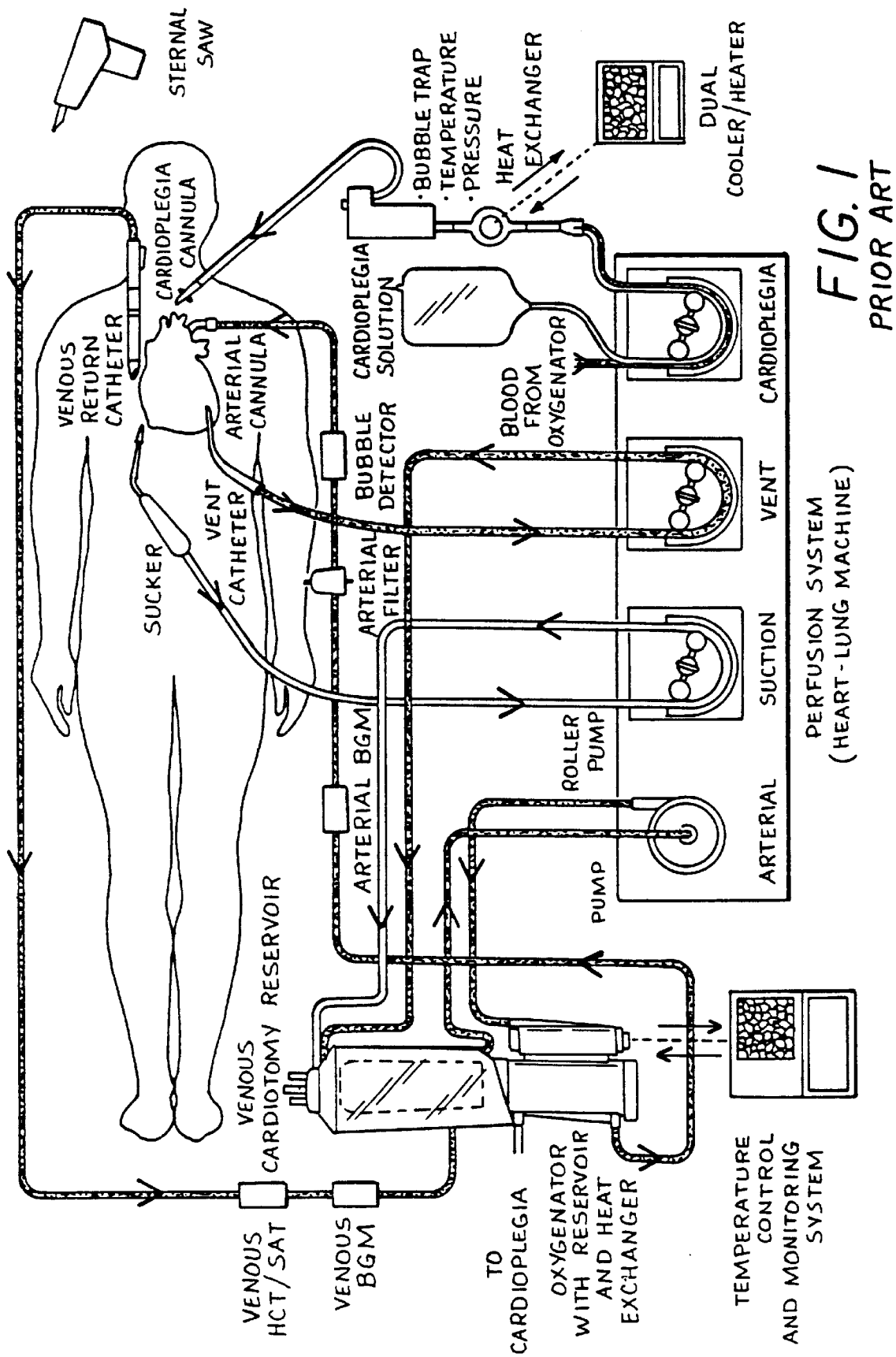
FIG. 1 is a schematic depiction of a cardiopulmonary bypass system of the prior art.
Figure 2:
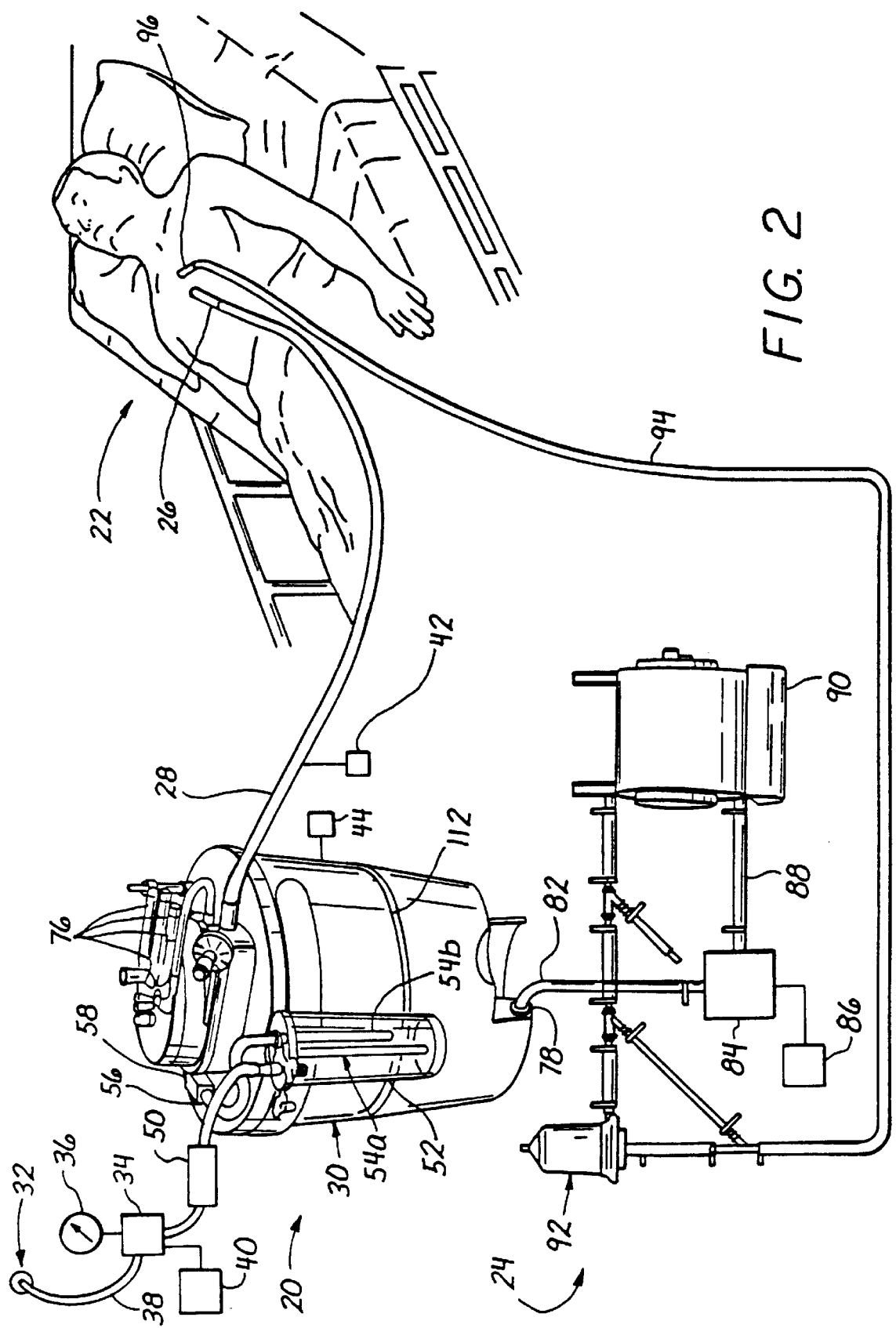
FIG. 2 is a schematic representation of a minimally invasive cardiopulmonary bypass system of the present invention utilizing a vacuum-assisted hard-shell venous reservoir.

With reference to FIG. 2, a vacuum-assisted venous drainage system 20 is illustrated connected to a patient 22 and shown as part of a larger cardiopulmonary bypass system 24. The patient 22 is placed on the cardiopulmonary bypass system 24 while undergoing a number of procedures, a minimally invasive heart surgery procedure is shown. In minimally invasive surgery, the chest cavity is not opened, but instead the various instruments and fluid communication conduits are inserted into the chest cavity through one or more small openings therein. Minimally invasive surgery greatly reduces the recovery time for such heart surgeries, and is rapidly gaining popularity in the medical community, and in the population at large. Although the present invention is illustrated in conjunction with minimally invasive surgery, similar advantages of reduced prime volume and less blood trauma are realized when using the invention in conjunction with more conventional open heart surgery techniques.

Hard Shell Reservoir Vacuum-Assisted Venous Drainage System

FIG. 2 illustrates a venous return cannula 26 extending into the patient's chest cavity and being connected on a proximal end to a venous return line 28. The venous return cannula 26 may be of a variety of configurations and sizes, but for minimally invasive surgery is preferably selected from a group of cannulas previously used for pediatric or small adult patients. For example, a typical large bore cannula for open heart surgery may have an OD 36 French on its tip, while cannulas for pediatric or small adult applications have tips of between 18 and 26 French. Such small bore cannulas are not presently used for conventional gravity impelled venous drainage in heart surgery on large adults because of their reduced volumetric flow capacity. With the present vacuum assisted drainage system 20, the cannulas 26 can be ever smaller in size, which facilitates the minimally invasive surgery techniques. In conjunction with the vacuum drainage system 20, modern thin-walled cannulas are preferably used which are fabricated by an extrusion manufacturing process, as opposed to a dipping process. Extruding the venous return cannula enables a thinner walled construction, and associated larger lumen size for any particular outer diameter. Such cannulas can be obtained from Research Medical Inc., of Salt Lake City, Utah, a subsidiary of Baxter International Inc. of Deerfield, Ill.

The vacuum assisted drainage system 20 comprises the aforementioned cannula 26 and return line 28, in combination with a venous reservoir 30 supplied with a negative pressure from a wall vacuum 32. A wall vacuum 32 is preferred, as almost all operating rooms already have such vacuum systems in place. Alternatively, however, those of skill in the art will understand that other sources of vacuum may be used. A vacuum regulator 34 and indicator 36 are provided in a vacuum line 38 between the wall vacuum 32 and the reservoir 30. The regulator 34 may be controlled by a controller 40 which receives input from sensors in various locations within the system 20. For example, a pressure sensor 42 may be provided in the venous return line 28 to sense overpressure caused by blockage in the line or cannula 26, or other such occlusion. Another sensor 44 may be provided to sense the pressure within the reservoir 30. In one specific example, the wall source 32 supplies negative pressure of approximately 170 mmHg, and the regulator 34 steps the negative pressure down to between 0 and 75 mmHg within the reservoir 30.

Between the vacuum regulator 34 and the reservoir 30, a combination pressure relief valve and vacuum stabilizer unit 50 is provided. The unit 50 may take a variety of forms, but provides the function of pressure relief if pressure within the reservoir 30 reaches a threshold value. In addition, the unit 50 provides the function of stabilizing the vacuum supplied to the reservoir 30 by resisting large changes in the magnitude of the vacuum. One particular embodiment of the combined pressure relief valve in vacuum stabilizer unit 50 is illustrated and described with respect to FIG. 7. Of course, the pressure relief valve and vacuum stabilizer may be provided separately and not as a unit.

Farther down the vacuum line 38 toward the reservoir 30, a moisture trap 52 is provided. The moisture trap 52 receives the vacuum line 38 at a nozzle in an upper end, which nozzle is in communication with a tube 54a extending downward into a chamber. A second tube 54b is in fluid communication with a second nozzle and shunt line 56. The shunt line continues from the moisture trap 52 to a vacuum port 58 provided in the reservoir 30. The moisture trap 52 collects any liquids or other fluid vapor escaping from the reservoir 30 so as not to contaminate the components in the vacuum line 38, or the wall vacuum 32. A number of moisture traps 52 are available, and the presently illustrated moisture trap attached rigidly to the reservoir 30 is a preferred form only.

Figure 3:
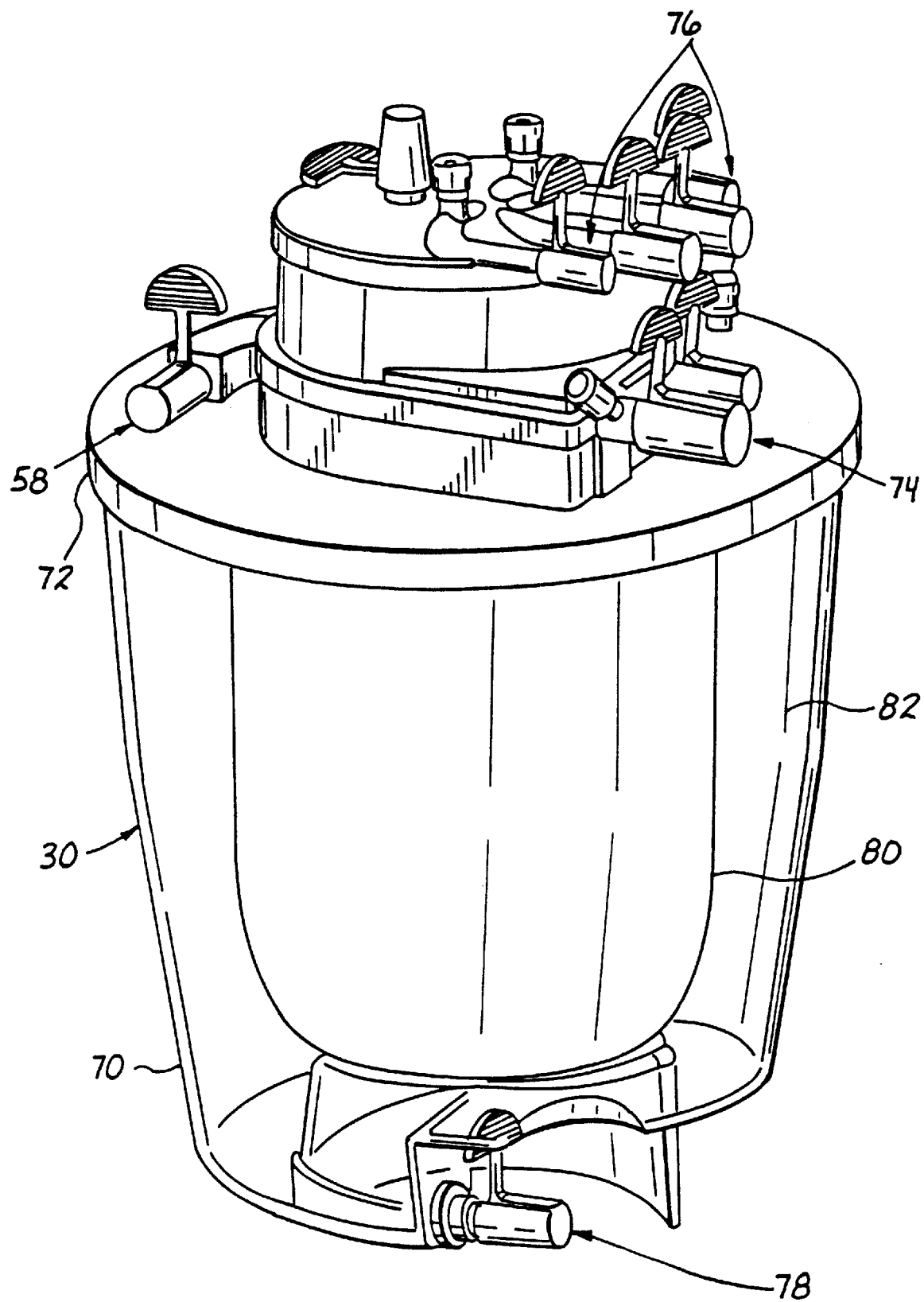
FIG. 3 is an enlarged perspective view of one type of hard-shelled reservoir which may be adapted for use with the present invention.

One particularly suitable reservoir 30 for use in the present vacuum assisted drainage system 20 is illustrated in FIG. 3. The reservoir 30 includes a hard shelled, generally cylindrical canister 70 which has a gradual outward taper in an upward direction. The reservoir shown is Model HSR 4000 manufactured by Bentley, Inc., of Irvine, Calif., a subsidiary of Baxter International Inc., of Deerfield, Ill. Other hard shelled reservoirs, such as the Bentley BMR-4500, may be suitable. The reservoir 30 includes a cap 72 having a plurality of ports communicating with the interior of the canister 70. More specifically, the reservoir 30 includes the vacuum port 58 and venous return port 74. A plurality of cardiotomy ports 76 on an upper housing may be attached to cardiotomy lines extending to the patient 22, although these lines are not shown for clarity. In a preferred embodiment, the vacuum assisted hard shelled system 20 is incorporated into a reservoir 30 such as the HSR 4000, which was previously used for gravity drainage. To facilitate gravity drainage, the vacuum port 58 was left open as a vent port to allow for the escape of air within the canister 70 as blood drains into the reservoir. In the present invention, a regulated vacuum source is connected to the vacuum port 58 so that the canister 70 is closed and sealed to the atmosphere, and the remaining components of the vacuum-assisted system 20 are implemented.

The preferred reservoir 30 is a combined cardiotomy and venous return reservoir, with concentric inner cardiotomy chamber, intermediate venous chamber, and outer collection chamber. These chambers can be seen in FIGS. 4 and 5, and are conventional in the art. In use, cardiotomy fluid along with any bone or particulate matter enters the inner cardiotomy chamber and is filtered before entering the intermediate venous chamber. With reference to FIG. 3, both the combined cardiotomy and venous blood is then passed through a defoamer sock 80 and into the outer collection chamber before exiting the reservoir through a lower exit port 78. The defoamer sock 80 comprises a generally cylindrical exterior shape which defines a space 82 with the canister wall 70.

With reference again to FIG. 2, the CPB circuit 24 also comprises a reservoir drain line 82 extending to a pump 84 controlled by a controller 86. The pump 84 may be of a variety of types, including roller pumps or centrifugal pumps. Blood is then pumped through a shunt line 88 to an oxygenator 90. Again, the oxygenator may take a variety of forms, but is preferably a SpiralGold oxygenator manufactured by Bentley, Inc. The oxygenated blood continues past an arterial filter 92 and to an arterial return line 94 terminating in an arterial cannula 96. Other components, such as bubble detectors, may be provided in the return line 94, as is well known in the art.

Vacuum-Assisted Venous Drainage Performance

The venous reservoir 30 is characterized by the hard outer shell 70 which is sufficient to withstand any pressures generated within from the wall vacuum 32 and regulator 34. The negative pressure developed within the hard shelled reservoir 30 creates a negative pressure within the venous return line 28, which in turn pulls blood from the vein in which the cannula 26 is placed. Because of the vacuum assisted venous return suction, the reservoir 30 may be positioned at various locations with respect to the patient 22. More specifically, as opposed to prior gravity drain reservoirs, the reservoir 30 may even be positioned above the patient 22, although a small elevation below the patient is preferred. Because the reservoir 30 need not be close to the ground, as before, it can be hung adjacent or behind the patient in various locations previously not possible. This greatly increases the flexibility of the operating room set up, and significantly reduces prime volume by reducing the length of tube from the cannula 26 to the reservoir 30.

Volumetric flow results for different cannula sizes, reservoir head heights below the patient, and vacuum magnitudes are presented below in several tables. These results were obtained using a Bentley HSR 4000 reservoir and a container of bovine blood. A roller pump is used to pump the blood from the reservoir back to the container of blood. The blood used had a hematocrit (HCT) level of about 32.5. The head height is the level of the reservoir below the container. The vacuum was connected to the conventional vent port, and all other input ports were plugged. The reservoir level was maintained at 2000 ml and measurements taken at steady state conditions. The range of blood flow through operating bypass systems varies, and a rough estimate for normal adults having a hematocrit level of 25–40 is between 3.5 and 4.5 lpm. It is apparent from these data, therefore, that flow rates sufficient for adult bypass surgery can be obtained with the vacuum-assisted reservoir system of the present invention using cannulas of reduced size. This development promises to revolutionize bypass procedures toward minimally invasive techniques.

TABLE I (Cannula Size = 24 Fr)

| | | | Pressure Measurements | |
|---|---|---|---|---|
| Head Height (inch) | Vacuum (mmHg) | Pump Flow (1 pm) | @ Cannula End (mmHg) | @ Reservoir End (mmHg) |
| 6 | 0 | 1.40 | −21 | 6 |
| 6 | −15 | 2.15 | −35 | −6 |
| 6 | −30 | 2.61 | −49 | −20 |
| 6 | −46 | 3.25 | −62 | −33 |
| 6 | −61 | 3.63 | −75 | −46 |
| 6 | −75 | 4.06 | −88 | −59 |
| 12 | 0 | 1.75 | −22 | 15 |
| 12 | −15 | 2.39 | −44 | −5 |
| 12 | −30 | 2.80 | −59 | −20 |
| 12 | −45 | 3.50 | −72 | −32 |
| 12 | −61 | 3.98 | −88 | −47 |
| 12 | −76 | 4.36 | −98 | −58 |
| 18 | 0 | 2.53 | −47 | 3 |
| 18 | −15 | 2.96 | −55 | −5 |
| 18 | −30 | 3.35 | −69 | −18 |
| 18 | −45 | 3.75 | −82 | −31 |
| 18 | −60 | 4.25 | −94 | −44 |
| 18 | −74 | 4.67 | −105 | −55 |

TABLE II (Cannula Size = 22 Fr)

| | | | Pressure Measurements | |
|---|---|---|---|---|
| Head Height (inch) | Vacuum (mmHg) | Pump Flow (1 pm) | @ Cannula End (mmHg) | @ Reservoir End (mmHg) |
| 6 | 0 | 1.10 | −18 | 6 |
| 6 | −15 | 1.53 | −32 | −7 |
| 6 | −30 | 1.91 | −46 | −20 |
| 6 | −45 | 2.31 | −59 | −32 |
| 6 | −60 | 2.63 | −72 | −45 |
| 6 | −75 | 2.98 | −85 | −57 |
| 12 | 0 | 1.62 | −34 | 3 |
| 12 | −15 | 1.87 | −44 | −6 |

TABLE II-continued (Cannula Size = 22 Fr)

| | | | Pressure Measurements | |
|---|---|---|---|---|
| Head Height (inch) | Vacuum (mmHg) | Pump Flow (1 pm) | @ Cannula End (mmHg) | @ Reservoir End (mmHg) |
| 12 | −30 | 2.28 | −58 | −19 |
| 12 | −45 | 2.64 | −72 | −33 |
| 12 | −60 | 2.97 | −83 | −45 |
| 12 | −75 | 3.26 | −98 | −58 |
| 18 | 0 | 1.75 | −41 | 7 |
| 18 | −15 | 2.18 | −55 | −6 |
| 18 | −30 | 2.56 | −70 | −19 |
| 18 | −45 | 2.82 | −82 | −32 |
| 18 | −60 | 3.15 | −95 | −44 |
| 18 | −75 | 3.52 | −109 | −57 |

TABLE III (Cannula Size = 20 Fr)

| | | | Pressure Measurements | |
|---|---|---|---|---|
| Head Height (inch) | Vacuum (mmHg) | Pump Flow (1 pm) | @ Cannula End (mmHg) | @ Reservoir End (mmHg) |
| 6 | 0 | .83 | −32 | 6 |
| 6 | −15 | 1.19 | −46 | −11 |
| 6 | −30 | 1.50 | −59 | −26 |
| 6 | −45 | 1.75 | −73 | −45 |
| 6 | −60 | 2.06 | −86 | −61 |
| 6 | −75 | 2.30 | −99 | −77 |
| 12 | 0 | 1.20 | −47 | −1 |
| 12 | −15 | 1.48 | −57 | −14 |
| 12 | −30 | 1.79 | −71 | −30 |
| 12 | −45 | 2.03 | −84 | −46 |
| 12 | −60 | 2.31 | −98 | −63 |
| 12 | −75 | 2.53 | −111 | −78 |
| 18 | 0 | 1.75 | −41 | 7 |
| 18 | −15 | 2.18 | −55 | −6 |
| 18 | −30 | 2.56 | −70 | −19 |
| 18 | −45 | 2.82 | −82 | −32 |
| 18 | −60 | 3.15 | −95 | −44 |
| 18 | −75 | 3.52 | −109 | −57 |

TABLE IV (Cannula Size = 18 Fr)

| | | | Pressure Measurements | |
|---|---|---|---|---|
| Head Height (inch) | Vacuum (mmHg) | Pump Flow (1 pm) | @ Cannula End (mmHg) | @ Reservoir End (mmHg) |
| 6 | 0 | .67 | −34 | 3 |
| 6 | −75 | 1.81 | −104 | −80 |
| 12 | 0 | .89 | −45 | 3 |
| 12 | −15 | 1.13 | −57 | −11 |
| 12 | −30 | 1.43 | −72 | −29 |
| 12 | −45 | 1.67 | −86 | −45 |
| 12 | −60 | 1.94 | −102 | −65 |
| 12 | −75 | 2.12 | −115 | −80 |
| 18 | 0 | 1.00 | −55 | 3 |
| 18 | −15 | 1.22 | −70 | −16 |
| 18 | −30 | 1.62 | −84 | −34 |
| 18 | −45 | 1.79 | −96 | −47 |
| 18 | −60 | 2.00 | −112 | −67 |
| 18 | −75 | 2.17 | −127 | −86 |

Reduced Blood/Air Interface

Hard shelled reservoirs are generally used when larger volumes, reduced resistance to venous return. and accurate blood volumes within the reservoir are needed. These units are typically larger than so-called "soft shell" reservoirs, and since the sides of the reservoir are rigid, flow is less restricted and volume levels at a certain liquid height can be measured and labeled on the reservoir. Hard shelled reservoirs, however, operate partially full so that a blood/air interface at the top of the liquid level exists. In contrast, soft shelled reservoirs are flexible and allow air to be excluded which substantially reduces the blood/air interface. Furthermore, the flexible nature of soft shell reservoirs restrict blood flow and the ability to directly measure the volume of blood within. The present invention provides for a direct visual volumetric measurement of blood while also reducing the blood/air interaction. Reducing blood/air interaction reduces the activation of blood and provides for less blood related complications during bypass surgery.

Figure 4A:
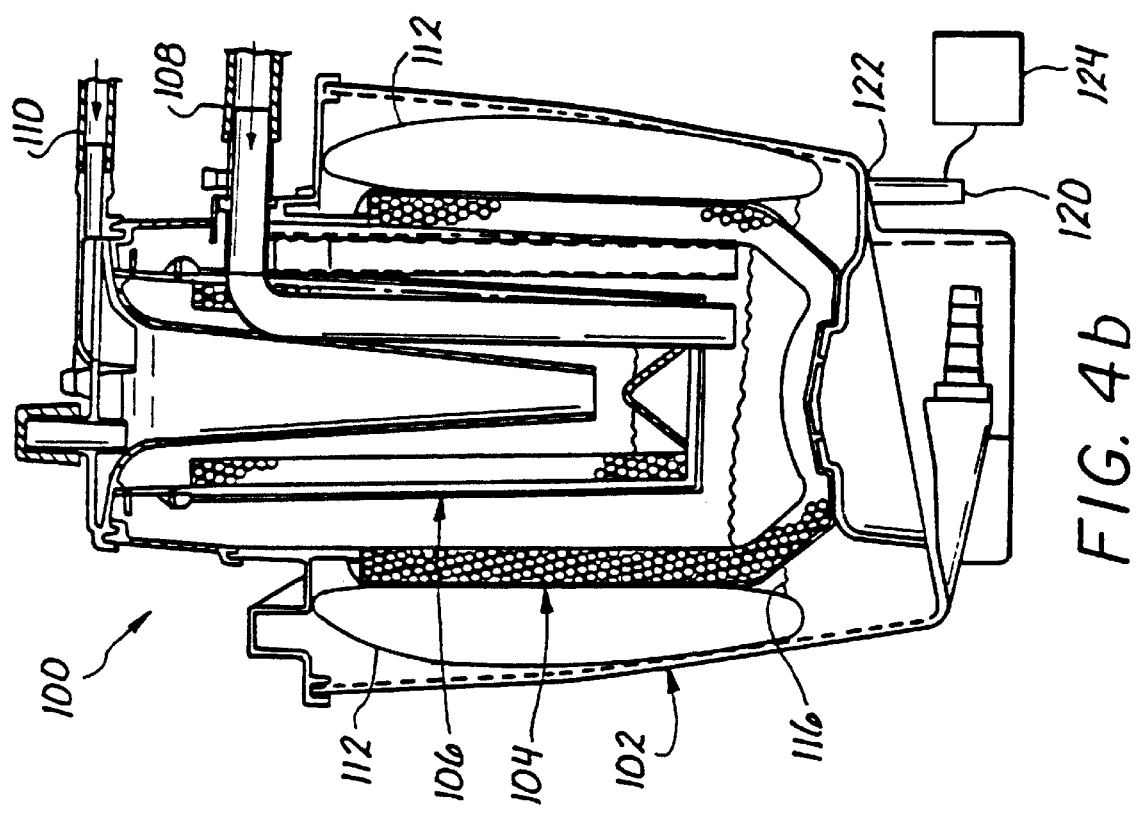
FIG. 4a is a cross-sectional view of a hard-shelled venous reservoir adapted for vacuum-assisted venous drainage and having reduce blood/air interface, prior to a vacuum being applied.
Figure 4B:
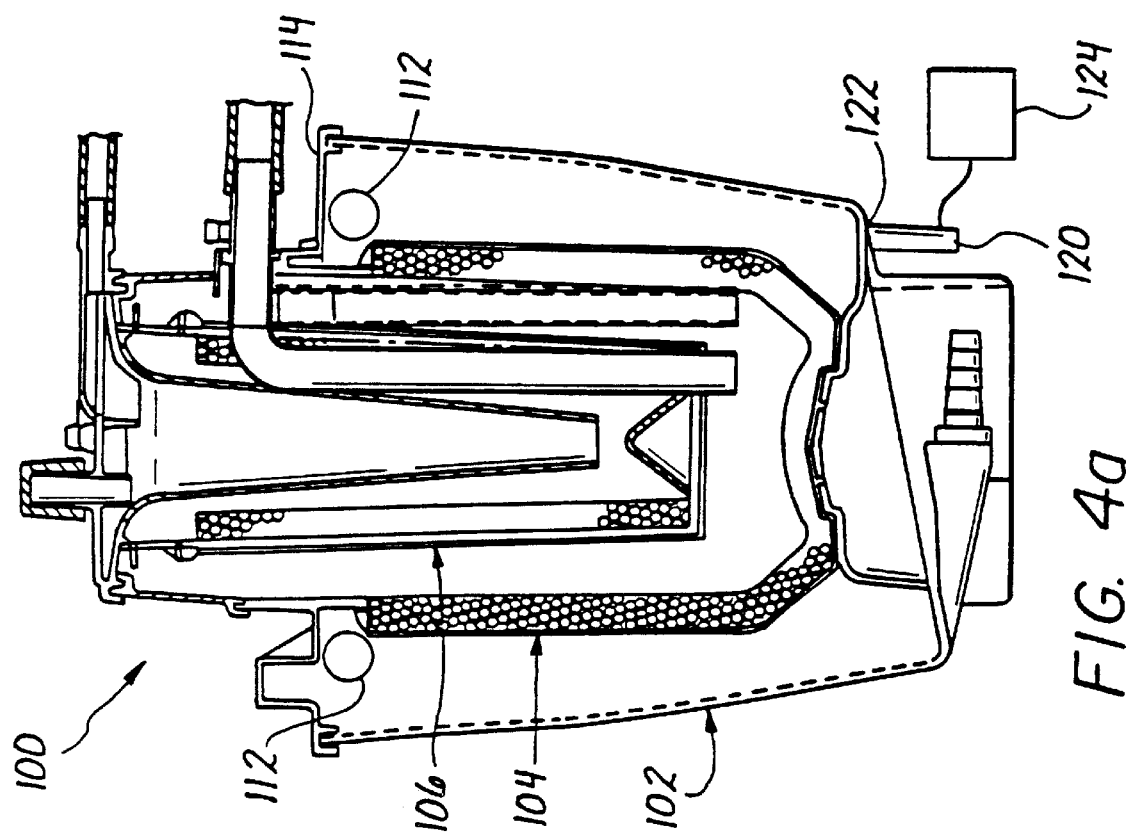
FIG. 4b is a cross-sectional view of the reservoir of FIG. 4a after a vacuum is applied.

With reference to FIGS. 4a and 4b, the present invention provides a hard shelled reservoir 100 which includes a mechanism for reducing the blood/air interaction, while also providing the benefits of a direct visual volume measurement. The reservoir 100 may be a modified HSR 4000 reservoir manufactured by Bentley, Inc., or other suitable hard shelled reservoir. In this respect, and as mentioned previously, the reservoir includes an outer canister 102, an inner venous canister 104, and an innermost cardiotomy canister 106. FIG. 4a on the left illustrates the reservoir 100 prior to any blood flow therethrough, while FIG. 4b shows blood entering through a venous return line 108, and fluid entering the cardiotomy canister 106 through a suction line 110. The reservoir 100 is supplied with a negative pressure, as described above with respect to FIGS. 2 and 3, although the vacuum port is not shown in these drawings.

To reduce the blood/air interface, a highly flexible, air impermeable membrane 112 is mounted in an upper area of the region between the outer canister 102 and the venous canister 104. In the illustrated embodiment, the membrane 112 comprises an annular tube of highly flexible material with a generatrix or circumferential edge being attached to the underside of the reservoir cap 114. The tubular membrane 112 may be attached by an adhesive, solvent bonding or other expedient methods. The tubular membrane 112 is constructed from a material such as a low durometer polyurethane or silicone, and is sufficiently flexible to expand and fill the inside of the reservoir 100 between the outer canister 102 and the venous canister 104 above a blood surface 116, as seen in FIG. 4b. Under atmospheric pressure, the tubular membrane should contain a small amount of air or inert gas within. The vacuum created within the reservoir 100 expands the tubular membrane 112 to fill the space above the blood surface 116. As the vacuum level in the reservoir 100 is varied leading to changes in blood level, the membrane 112 will expand or contract and maintain contact with the surface of the blood without significantly hindering flow. Preferably, the membrane 112 is configured to contact substantially all of the surface of the blood in the annular space outside of the venous canister 104. This essentially limits blood/air contact and associated blood related complications to the spaces within the venous canister 104.

Figure 5B:
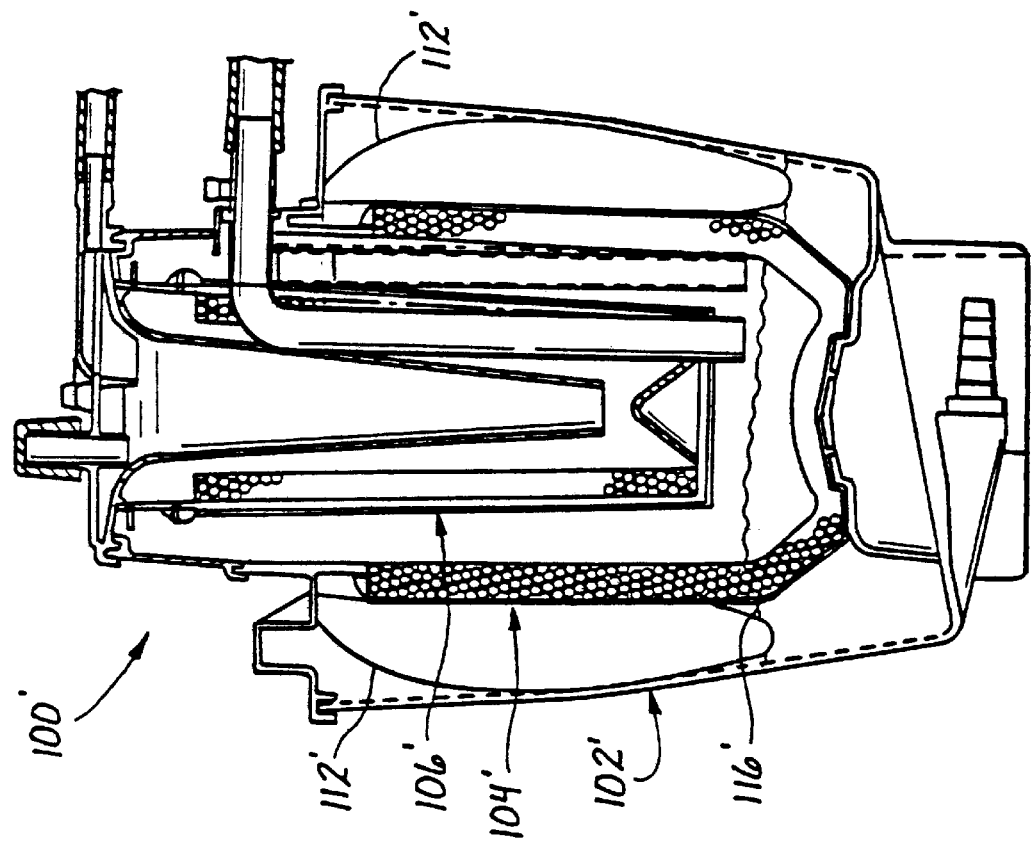
FIG. 5b is a cross-sectional view of the reservoir of FIG. 5a after a vacuum is applied.
Figure 5A:
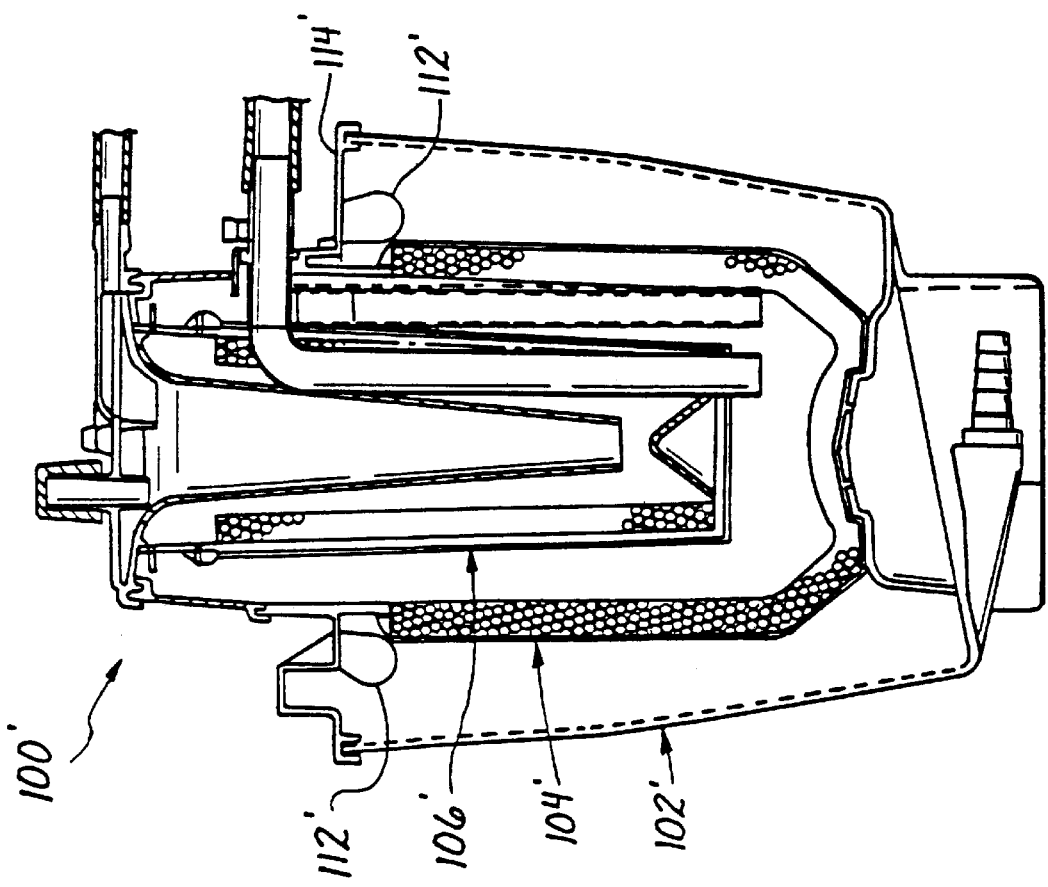
FIG. 5a is a cross-sectional view of another embodiment of a hard-shelled venous reservoir adapted for vacuum-assisted venous drainage and having reduce blood/air interface, prior to a vacuum being applied.

FIGS. 5a and 5b illustrate another hard shelled reservoir 100' which is configured identically to the reservoir 100 described in FIG. 4. Common components of the reservoir 100' are thus indicated by a prime. A flexible air impermeable membrane 112' is substituted for the tubular membrane 112 shown in FIG. 4a. Instead of being a contained tube, the membrane 112' is formed of a sheet of highly flexible material with its longitudinal edges attached to the underside of the cap 114'. In all other respects, the flexible membrane 112' acts in the same manner as the earlier described tubular membrane, and expands as in FIG. 5b to substantially fill the space between the outer canister 102' and the venous canister 104'. Again, this substantially reduces the blood/air interface within the reservoir 100'.

FIGS. 4a and 4b also illustrate a system for accurately determining the volume of blood within the reservoir. The system comprises an ultrasonic sensor 120 mounted to a lower wall 122 of the canister 102. The sensor 120 is mounted to be directly underneath the space between the outer canister 102 and the venous canister 104. The sensor 120 provides information to a control system 124 which may be in communication with control systems for the vacuum generator, or blood pump, such as the controls 40 and 86 illustrated in FIG. 2. The sensor detects the level of blood within the reservoir 100, such as the blood surface 116 in FIG. 4b, and sends that information to a processor which is able to compute the volume of blood in the reservoir. Such a sensor is shown and described in U.S. Pat. Nos. 5,303,585 and 5,586,085, both to Lichte. Accurate knowledge of the blood level within the reservoir 100 enables rapid response to varying blood flow conditions so that the vacuum may be adjusted to increase or decrease the flow, or for other purposes such as metering an anticoagulant added to the extracorporeal blood to reduce clotting.

Soft Shell Reservoir Vacuum-Assisted Venous Drainage System

Figure 6:
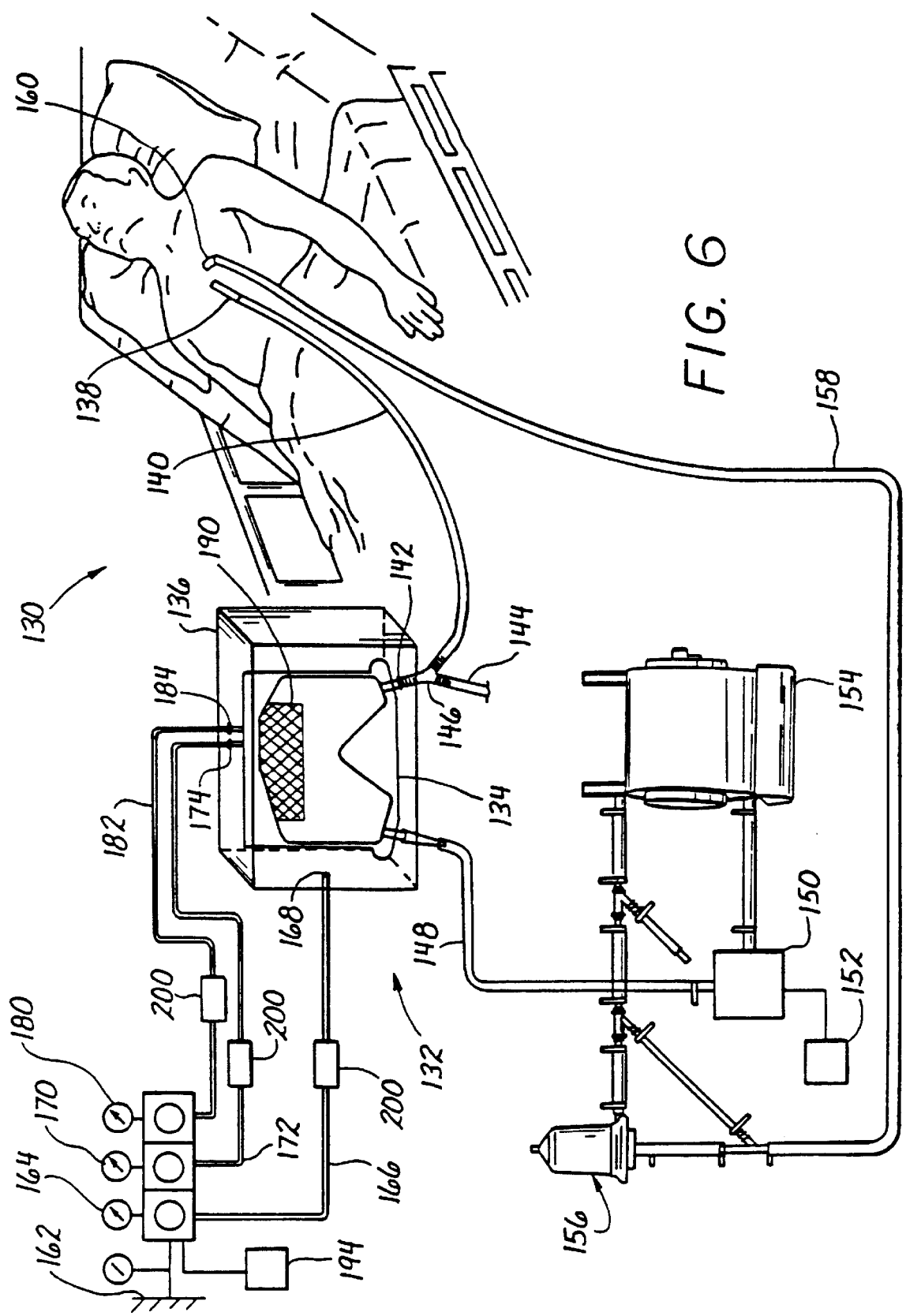
FIG. 6 is a schematic representation of a further embodiment of a minimally invasive cardiopulmonary bypass system of the present invention utilizing a vacuum-assisted soft-shell venous reservoir.

With reference to FIG. 6, a CPB procedure 130 is shown utilizing a soft shell reservoir venous drain system 132. The system 132 includes a soft shell reservoir 134 located completely within a rigid housing 136. A venous cannula 138 placed in a vein of the patient is in fluid communication with the reservoir 134 via a venous return line 140. The return line 140 enters the housing 136 through a sealed aperture 142. A cardiotomy line 144 leading from a cardiotomy filter (not shown) may be joined to the venous return line at a Y-junction 146. A drain line 148 connects the output of the reservoir 134 with a pump 150, which may have a controller 152. The pump 150 sends blood through an oxygenator 154, an arterial filter 156, an arterial line 158, and finally to an arterial cannula 160 for perfusing the patient's arterial system.

The blood from the venous system is pulled into the reservoir 134 by a negative pressure gradient in the venous return line 140 created by a negative pressure in the reservoir. A source of vacuum 162, such as a wall vacuum, is connected to the interior of the housing 136 via a pressure regulator 164 and vacuum line 166. The vacuum line 166 projects through a sealed fitting 168 into the housing 136. A negative pressure created in the housing 136 tends to inflate the reservoir 134 which in turn, creates a vacuum therein to draw the venous blood from the patient. The reservoir 134 may be of a variety of types, but is preferably one of the following made by Bentley, Inc: BMR-800 Gold or BMR-1900 Gold.

A second pressure regulator 170 communicates with the interior of the reservoir 134 via a conduit 172 entering the housing 136 through a sealed fitting 174. The pressure within the conduit 172 is regulated to maintain a pressure differential between the interior and exterior of the reservoir. This secondary pressure regulation may be used to adjust venous return flow rates.

A third pressure regulator 180 communicates with the interior of the reservoir 134 via a conduit 182 entering the housing 136 through a sealed fitting 184. The pressure within the conduit 182 is regulated to gently pull a suction at the very top of the reservoir 134 to remove any air which may be trapped within. Microbubbles in the blood sometimes combine to form significant air pockets which must be removed before the blood is sent back to the patient. Further, the blood/air interface is detrimental and is preferably eliminated.

As an alternative to the air removal conduit 182, a membrane 190 of sandwiched layers of hydrophobic and hydrophilic materials may be formed into the upper wall of the reservoir 134. This membrane 190 would facilitate passive venting of air from the reservoir 134 due to the vacuum generated within the housing 136.

As with the earlier described hard shell reservoir embodiment, various sensors may be positioned around the system 130 for monitoring pressures, flows, temperatures, blood levels, etc. A microprocessor 194 may be provided to control the three pressure regulators 164, 170, and 180 and enhance the efficiency of the system. The microprocessor 194 may also be connected to the pump controller 152, oxygenator 154, or other device such as a heat exchanger (not shown).

Pressure Relief Valve/Vacuum Stabilizer

Figure 7:
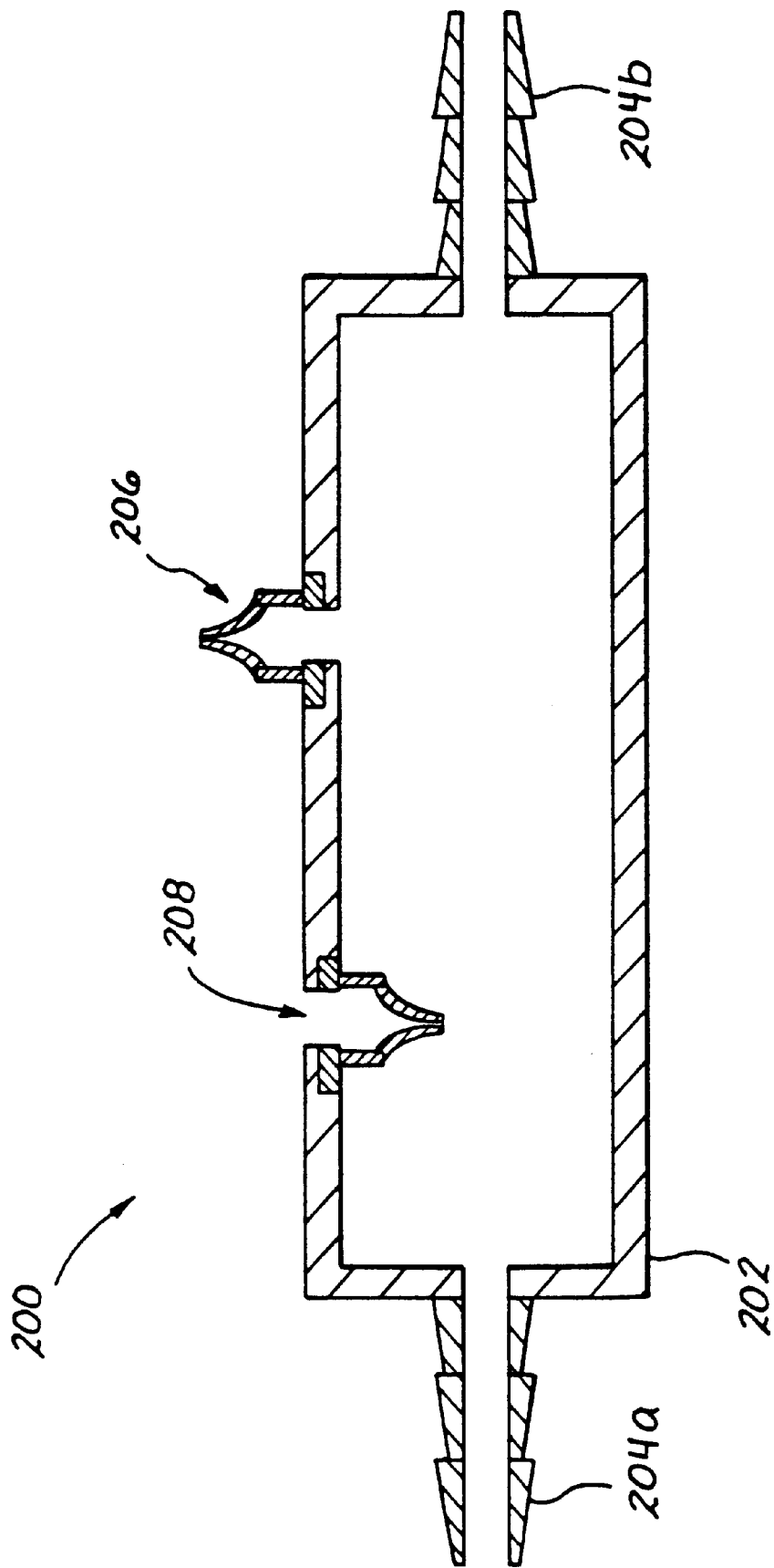
FIG. 7 is a schematic representation of a combination pressure-relief valve and vacuum stabilizing device for use with vacuum-assisted reservoirs of the present invention.

Each of the conduits 166, 172 and 182 between the vacuum regulators and housing 136 include a pressure relief and vacuum stabilizer unit 200, a preferred form of which is illustrated in FIG. 7. The unit 200 comprises a chamber 202 open at opposite ends to nipples 204a and 204b. The nipples 204a,b are used to connect the units 200 in series in one of the conduits 166, 172 and 182. The unit 200 further includes a pressure relief valve 206 and a vacuum stabilizing valve 208. The pressure relief valve 206 cracks open at a very low pressure differential threshold and bleeds air out of the line, in response to buildup of positive pressure. The vacuum stabilizing valve 208 continuously bleeds air into the system at a flow rate proportional to the level of vacuum to be maintained by the particular pressure regulator 164, 170 or 180. When the level of vacuum increases within the system to a predetermined threshold value, the vacuum stabilizing valve 208 yields (the opening increases) proportionately to allow an increased amount of air to bleed into the system, thereby compensating for the increased level of vacuum. This helps reduce large swings in vacuum, thus the stabilizing effect. In a preferred form, both the pressure relief valve 206 and a vacuum stabilizing valve 208 are conventional duckbill valves chosen for the desired pressure threshold. This greatly reduces the cost of the system.

Key Hole Surgery

Figure 8:
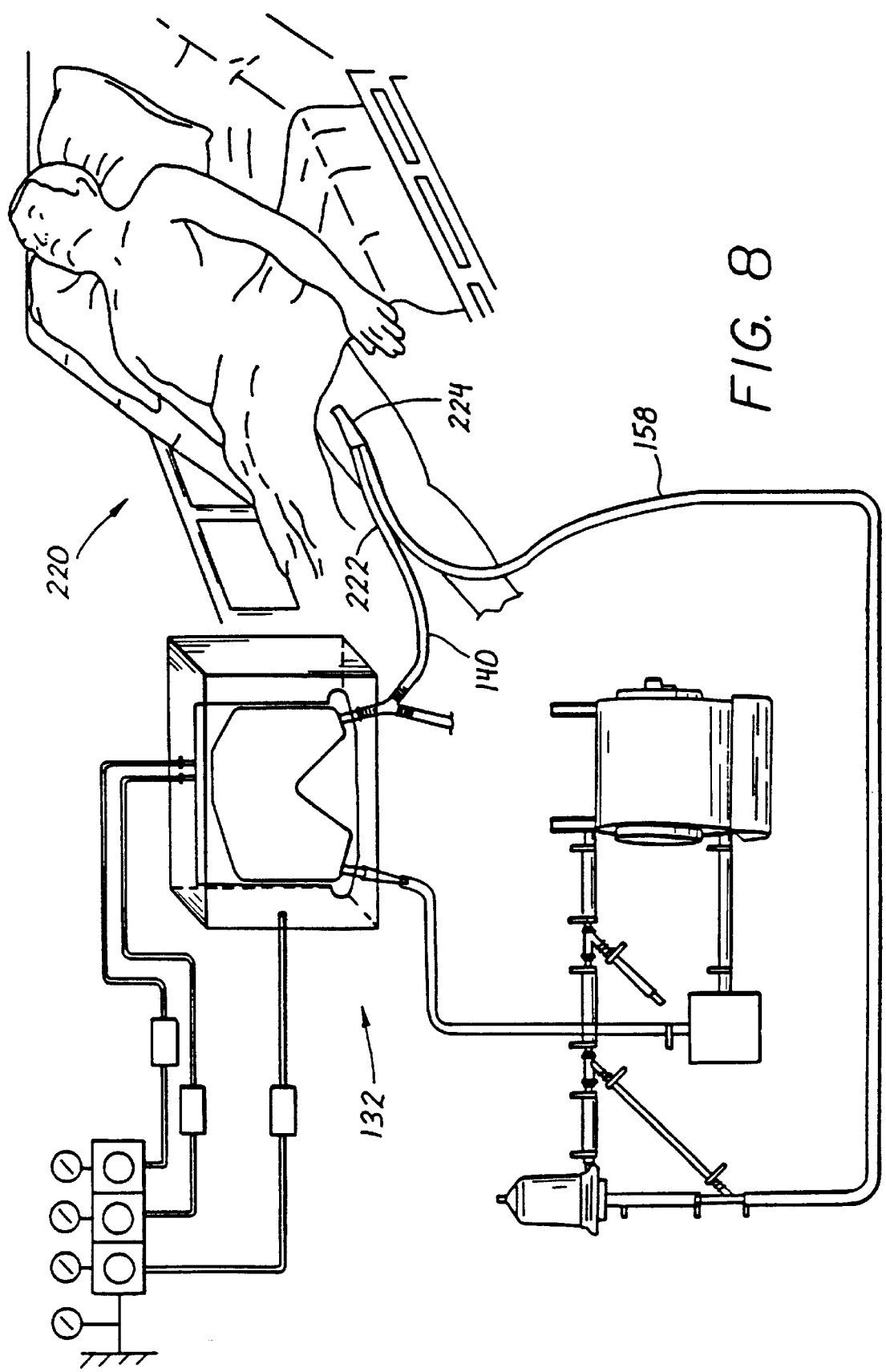
FIG. 8 is a schematic representation of a further embodiment of a minimally invasive cardiopulmonary bypass system of the present invention utilizing a vacuum-assisted soft-shell venous reservoir.

One type of minimally invasive surgery gaining in acceptance is a so-called "key hole" technique 220 shown in FIG. 8. A vacuum-assisted soft shell reservoir system 132, as shown and described with reference to FIG. 6, is connected to a patient with the venous return line 140 and arterial perfusion line 158 joining at 222. The two lines are introduced into the patients femoral vein using a dual-stage cannula 224. The arterial perfusion line 158 extends up through the patient's vasculature to a location suitable for oxygenated blood perfusion. With this type of surgery, only one access incision is needed, and the perfusion lines are positioned out of the way of the patient's thorax, where other instruments or probes may be inserted to operate on the heart.

Flow Control

The pressure differential created by the application of a negative pressure at the reservoir end of the venous return line can be regulated to enable control over venous return, independent of the relative positioning of the reservoir to the operating table. As mentioned above, various sensors may be positioned at critical locations for measuring pressure, temperature, flow rates, blood levels, etc. The sensors may be connected to a control system with output to a number of actuators such as the vacuum regulators, circulation pump, secondary regulators, heat exchangers, etc. Certain variables can be sensed and/or controlled with appropriate feedback loops, preferably coded into a programmable microprocessor. These variables include the amount of vacuum applied to the reservoir (or housing around the reservoir), the pump speed or pulse rate, the threshold level of vacuum allowed in the venous return line, and the reservoir minimum and maximum volumes. Such a sophisticated control system would result in reduced hemodilution (prime volume) by enabling reduced cannula sizes, reduced tubing sizes and lengths, accurate control of venous drainage, and enhanced control of arterial return. In addition, benefits gained to perfusion control include positive control of venous drainage and arterial perfusion, and microprocessor control of flow rates. In addition, the microprocessor could be adapted to measure and control circuit temperature and oxygenation. With adequate fail-safes built into the system, the traditional role of the perfusionist is greatly reduced.

Pediatric Applications

Although cannula sizes for older children and teens range from 18–26 Fr, smaller cannulas are often used for infants and newborns. For example, Research Medical, Inc. (RMI), of Salt Lake City, Utah, provides a line of cannulas down to 8 Fr in size. French (Fr) is a term for the outside diameter (OD) of the cannula, and the conversion to metric is: 1 mm=πFr. Thus, an 8 Fr cannula has an OD of 2.54 mm. The bore size of a particular Fr cannula will depend on the cannula wall thickness. As mentioned above, RMI has developed an extrusion process which brings the wall thickness of an 18 Fr cannula down to 0.018 inch (0.457 mm) from between 0.022–0.027 inch (0.559–0.686 mm) for earlier designs fabricated by conventional dipping methods. An 18 Fr cannula has an OD of 5.73 mm. With a wall thickness of 0.457 mm, the ID is 4.816 mm. Conventional 18 Fr cannulas would have a maximum ID of 4.612 mm. The increase in the cross-sectional flow area through extruded cannulas is thus 9%. This increase, in combination with drawing a negative pressure in the cannula, greatly facilitates the use of smaller and smaller cannulas. It should be emphasized that cannulas smaller than the currently available 8 Fr size may become viable for neonatal care, for example, with the vacuum-assisted drainage and thin walled cannulas. In other words, the benefits of the present invention will be realized by patients of all sizes. Moreover, the reduction in extracorporeal blood prime volume which is realized by locating the reservoir closer to the vein is most significant for neonatals and infants, who have a relatively much less amount of blood in their vasculatures. Neonatals, for example, may only require a blood flow through the CPB circuit of less than 1 lpm.

Benefits to Vacuum-Assisted Venous Drainage

The present invention is expected to achieve the following benefits for conventional cardiopulmonary bypass surgery:

1. Venous return flow rates will no longer depend on the physical location of the reservoir with respect to the operating table, providing opportunities for miniaturization of the entire CPB circuit.
2. A miniaturization of the CPB circuit would lead to minimizing blood contact with foreign surfaces thereby reducing complications associated with immune response such as platelet depletion, complement activation and leukocyte activation.
3. Since venous flow is initiated by the application of negative pressure, the venous return line need not be primed. This leads to a substantial reduction in priming volume of the CPB circuit, resulting in reduced hemodilution of the patient. This aids in the recovery of the patients physiological status after surgery.

4. Surgeon acceptance of the use of vacuum for venous return, could lead to suction systems taking the place of roller pumps in other applications. This potentially could lead to elimination of roller pumps that support the sucker, sump and vent functions that fall under the responsibility of the perfusionist. This would result in minimizing blood trauma caused by roller pumps. Additionally, this would also free-up valuable floor space in the vicinity of the operating table.

In addition, the present invention is expected to achieve the following benefits for Minimally Invasive Surgery:

1. Vacuum assist will help achieve higher flow rates through smaller cannulae. This will allow the use of smaller cannulae thereby providing the surgeon greater access to the site of the surgery. This could also potentially eliminate the need for larger size cannulae.

2. MICS techniques, such as the Key Hole concept, use the femoral vein as access port for CPB circuitry. This technique imposes stringent limitations on the cross-section and length of the catheter/cannula used for venous return. Vacuum assist can replace centrifugal pumps to enhance venous drainage in these applications.

It is understood that the examples and embodiments described herein and shown in the drawings represent only the presently preferred embodiments of the invention, and are not intended to exhaustively describe in detail all possible embodiments in which the invention may take physical form. Indeed, various modifications and additions may be made to such embodiments without departing from the spirit and scope of the invention.

What is claimed is:

1. A vacuum assisted venous reservoir, comprising:

a rigid, sealed housing, said housing being sealed such that a relative vacuum can be maintained between the interior and the exterior of the housing;

a flexible, blood impermeable reservoir positioned within the interior of the housing;

an inlet port in communication with the interior of the reservoir;

a venous blood conduit attached to the inlet port and in communication with the interior of the reservoir, the venous blood conduit passing through a first sealed opening in the housing and being connected to a source of venous blood such that venous blood can pass from the source of venous blood to the interior of the reservoir;

a vacuum conduit extending through a second sealed opening in the housing, the vacuum conduit being in communication with a source of vacuum and the interior of the housing such that vacuum pressure can be applied to the interior of the housing;

a pressure regulator in communication with the vacuum conduit and vacuum source for regulating the vacuum pressure in the interior of the housing;

a second vacuum conduit extending through a third sealed opening in the housing and in communication with a source of vacuum and the interior of the reservoir such that vacuum pressure can be applied to the interior of the reservoir; and a second pressure regulator in communication with the second conduit and the second vacuum source for regulating the vacuum pressure in the interior of the reservoir.

2. The reservoir of claim 1, further including a membrane formed into a wall of the reservoir, said membrane being configured to vent air from the interior of the reservoir.

3. The reservoir of claim 2, whereby said membrane is made of sandwiched layers of hydrophobic and hydrophilic materials.

4. The reservoir of claim 1, wherein the flexible reservoir further includes an air permeable membrane for venting air from within the reservoir to the interior of the housing.

5. The reservoir of claim 1, wherein the second vacuum conduit communicates with the uppoermost portion of the interior of the reservoir such that vacuum pressure applied to the interior via the second vacuum conduit can remove air trapped within the reservoir.

* * * * *